United States Patent [19]

Sowinski et al.

[11] 4,022,774

[45] May 10, 1977

[54] 1,2,4-BENZOTHIADIAZINES

[75] Inventors: Francis Alexander Sowinski, Edison, N.J.; B. Richard Vogt, Yardley, Pa.

[73] Assignee: E. R. Squibb & Sons, Inc., Princeton, N.J.

[22] Filed: Sept. 22, 1975

[21] Appl. No.: 615,435

Related U.S. Application Data

[62] Division of Ser. No. 411,547, Oct. 31, 1973, Pat. No. 3,926,977.

[52] U.S. Cl. .............................. 260/243 D; 424/246
[51] Int. Cl.² .............. C07D 285/22; C07D 285/24
[58] Field of Search ................................ 260/243 D

[56] References Cited

OTHER PUBLICATIONS

Cohnen et al., *Chem. Ber* 105 757–769 (1972).
Barnes et al., *JCS Chem. Comm* 1973 (20), 765, 776–777, Oct. 24, 1973.

*Primary Examiner*—Nicholas S. Rizzo
*Attorney, Agent, or Firm*—Lawrence S. Levinson; Merle J. Smith; Donald J. Barrack

[57] ABSTRACT

Novel 1,2,4-benzothiadiazines substituted by an oxo group in the 3-position and substituted in the 4-position with hydrogen, lower alkyl, amino-lower alkyl, mono- or di-lower alkyl amino-lower alkyl, or imino-lower alkyl, are useful as central nervous system depressants, and as diuretics.

4 Claims, No Drawings

1,2,4-BENZOTHIADIAZINES

This application is a division of copending U.S. patent application Ser. No. 411,547 filed Oct. 31, 1973, and now U.S. Pat. No. 3,926,977, issued Dec. 16, 1975.

BRIEF DESCRIPTION OF THE INVENTION

Compounds having the structure:

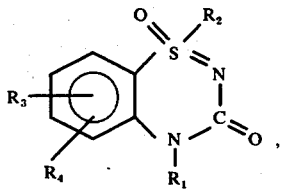

and their pharmaceutically acceptable acid-addition salts, have useful pharmacological activities. In formula I, and throughout the specification, the symbols are as defined below:

$R_1$ is lower alkyl; amino-lower alkyl; mono- or di-lower alkyl amino-lower alkyl; or imino-lower alkyl wherein the imino group as the formula

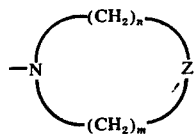

where
Z is oxygen,

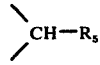

($R_5$ is hydrogen, phenyl, or benzyl), or

($R_6$ is hydrogen, lower alkyl, phenyl, or phenyl substituted with halogen, lower alkyl, lower alkoxy, or trifluoromethyl), $n$ is 1, 2 or 3, and $m$ is 2 or 3;

$R_2$ is phenyl or phenyl substituted with halogen, nitro, trifluoromethyl, lower alkyl, or lower alkoxy;

$R_3$ is hydrogen, halogen, nitro, cyano, trifluoromethyl, lower alkyl, or lower alkoxy; and $R_4$ is hydrogen or

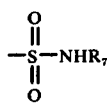

($R_7$ is hydrogen or lower alkyl).

The term "lower alkyl" refers to alkyl groups having 1 to 8 carbon atoms. The alkyl groups may be either straight chained or branched, e.g., methyl, ethyl, propyl, isopropyl, tert-butyl, pentyl, isooctyl, and the like.

The term "lower alkoxy" refers to groups having the formula Y—O— wherein Y is lower alkyl as defined above.

The term "halogen" refers to fluorine, chlorine, bromine, and iodine.

Exemplary of the heterocyclic moieties contemplated by the formula

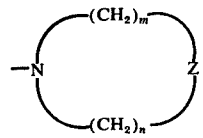

are aziridinyl, azetidinyl, diazetidinyl, oxazetidinyl, isoxazolindinyl, imidazolyl, pyrrolidino, piperidino, piperazino, $N^4$-alkylpiperazino, $N^4$-phenylpiperazino, morpholino, pyrimidinyl, azepinyl, octahydroazocinyl, etc. The 5 and 6 membered rings are preferred.

DETAILED DESCRIPTION OF THE INVENTION

The compounds of formula I, wherein $R_1$ is other than lower alkyl, are central nervous system depressants and may be used as tranquilizers for the relief of anxiety and tension states, for example in mice, rats, dogs and other mammalian species, in the same manner as chlordiazepoxide. For this purpose these compounds may be incorporated in a conventional dosage form such as tablet, capsule, injectable or the like, along with the necessary carrier material, excipient, lubricant, buffer or the like, for oral or parenteral administration in single or divided doses of about 1 to 100 mg./kg./day, preferably about 5 to 15 mg./kg., two to four times daily.

The compounds of formula I are diuretics, and as such, are useful in the treatment of hypertension in mammals. They may be formulated in conventional dosage form such as tablet, capsule, injectable or the like, along with the necessary carrier material, excipient, lubricant, buffer or the like, for oral or parenteral administration in single or divided doses of from about 1 to 100 mg./kg./day, preferably 3 to 12 mg./kg./day.

The compounds of formula I wherein $R_4$ is hydrogen are prepared using acids having the formula:

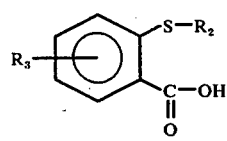

as the starting material. Compounds of formula II are known; see, for example, Coll. Czech. Chem. Commun., 33, 1852 (1968), J. Org. Chem., 38, 20 (1973) and references cited therein.

The acid of formula II is converted to the corresponding acid chloride having the formula:

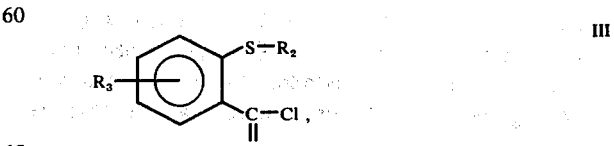

using means well known in the art. For example, an acid of formula II may be reacted with either thionyl chloride, phosphorous trichloride, or phosphorous pentachloride. The conversion may be carried out in an organic solvent, e.g., benzene, at elevated temperatures.

The acid chloride of formula III can be converted to an acetophenone derivative having the formula:

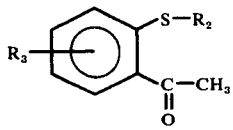
IV by reacting it with ethoxy-magnesium diethyl malonate in an inert organic solvent, such as ethyl ether, under reflux conditions for a period of time ranging from about 1 hour to 24 hours, preferably 2 hours to 4 hours, and subsequently hydrolyzing the resulting complex with sulfuric acid and heating to decarboxylate the intermediate acylation product.

The compound of formula IV is oxidized to the corresponding sulfoxide, i.e.,

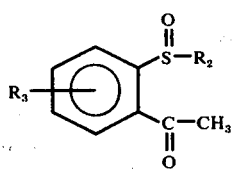
V using a mild, selective oxidizing agent such as sodium periodate. The oxidation reaction is run at a temperature of from about 0° C to 85° C, preferably 30° C to 50° C, for about 24 hours to 15 days, preferably 5 days to 7 days, in an organic solvent such as glyme.

Reaction of the 2-(substituted sulfinyl)acetophenone of formula V with hydrazoic acid yields a mixture of products having the formulas:

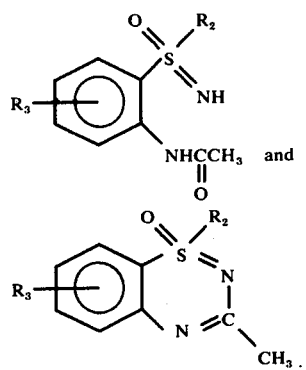
VI

VII

The reaction is run in an organic solvent, preferably a halogenated hydrocarbon such as chloroform, at a temperature of from about −30° C to +55° C, preferably 30° C to 50° C. In addition to the hydrazoic acid, a strong mineral acid such as sulfuric acid, is also present.

The product mixture made up of compounds of formulas VI and VII is hydrolized to yield a 2-(substituted sulfonimidoyl) aniline derivative having the formula:

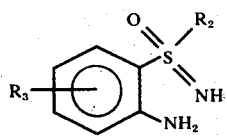
VIII

The hydrolysis reaction is carried out under reflux conditions in an aqueous solution of base such as sodium or potassium hydroxide. The compound of formula VIII is converted into an acid-addition salt, preferably one that is physiologically acceptable. Exemplary salts are the hydrohalides, sulfate, nitrate, phosphate, tartrate, maleate, fumarate, citrate, succinate, methanesulfonate, benzenesulfonate, toluenesulfonate and the like.

Ring closure of the acid-addition salt of the compound of formula VIII is accomplished by reacting the salt with 1,1′-carbonyldiimidazole in an inert organic solvent, such as o-dichlorobenzene at reflux temperature for about 1 hour to 24 hours, preferably 1 hour to 3 hours. The resulting compound has the structure:

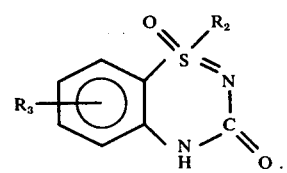
IX

Compounds of formula IX are novel intermediates and as such they constitute a part of this invention.

Reaction of the substituted 1,2,4-benzothiadiazin-3(4H)-one, 1-oxide of formula IX with a compound of the formula:

$R_1$—X    (X)

wherein X is halogen, preferably chlorine, bromine or iodine, yields a compound of formula I wherein $R_4$ is hydrogen. The substituted 1,2,4-benzothiadiazin-3(4H)-one, 1-oxide of formula IX is suspended in glyme, and sodium hydride is added to the suspension at a temperature of about −5° C to 85° C, preferably 0° C to 5° C, followed by the addition of the compound of formula X. After the compound of formula X has been slowly added, the reaction mixture is heated at reflux for about 1 hour to 24 hours, preferably 3 hours to 8 hours.

Compounds of formula I wherein $R_4$ is

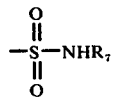

are obtained using compounds of the formula:

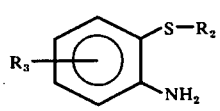
XI as starting materials. The compounds of formula XI are prepared using methods described in Chem. Ber., 39, 3597ff(1906) and in United States Pat. No. 3,188,320 issued June 8, 1965 to Sowinski et al.

The aniline derivative of formula XI is first reacted with acetic anhydride under reflux conditions for about 5 minutes to 8 hours, preferably 15 minutes to 1 hour. The reaction is run in an organic solvent, preferably a halogenated hydrocarbon such as chloroform. A base such as pyridine is added to the reaction mixture. The resulting acetanilide has the formula:

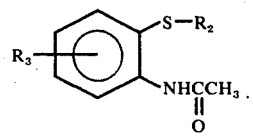

XII

The acetanilide of formula XII is reacted with chlorosulfonic acid in an organic solvent such as o-dichlorobenzene at a temperature of from about 0° C to 180° C, preferably 120° C to 150° C for a period of time ranging from about 10 minutes to 16 hours, preferably 1 hour to 3 hours, and yields a chlorosulfonyl substituted acetanilide having the formula:

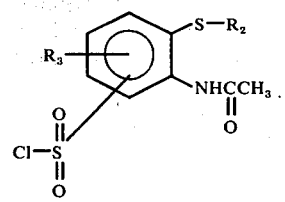

XIII

The compound of formula XIII is dissolved in an aromatic hydrocarbon, such as benzene, and added slowly to a concentrated solution of aqueous ammonia. The chlorosulfonyl acetanilide solution, is added to the ammonia at a temperature of from about 0° C to 80° C, preferably 5° C to 10° C. After the addition is completed, the reaction mixture is heated to reflux temperature and then stirred for a period of time ranging from about 1 hour to 24 hours, preferably 1 hour to 3 hours. The product obtained has the formula:

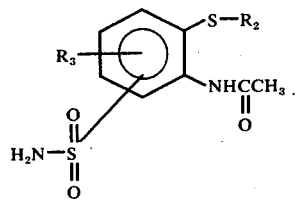

XIV

The sulfamylacetanilide of formula XIV is oxidized using a mild, selective oxidizing agent such as sodium periodate to yield a compound of the formula:

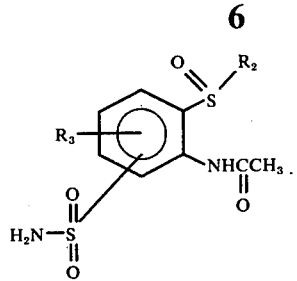

XV

Reaction may be carried out in glyme by slowly adding an aqueous solution of the oxidizing agent to the sulfamylacetanilide. Following completion of the addition of the oxidizing agent, the mixture is stirred for a period of time ranging from 24 hours to 240 hours, preferably 72 hours to 120 hours, while heating under reflux conditions.

The compound of formula XV is hydrolized using an aqueous solution of base such as potassium or sodium hydroxide. The compound of formula XV is dissolved in an aqueous base and heated at reflux temperature for a period of time ranging from 1 hour to 5 hours, preferably 2 hours to 4 hours. The product has the formula:

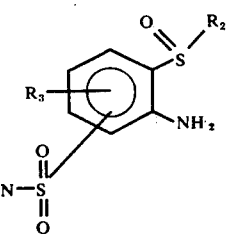

XVI

The compound of formula XVI is reacted with hydrazoic acid in an organic solvent, preferably a halogenated hydrocarbon such as chloroform, at a temperature of from about −30° C to 55° C, preferably 30° C to 50° C. In addition to the hydrazoic acid, a mineral acid such as sulfuric acid, is also present. The resultant product has the formula:

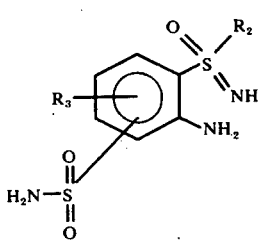

XVII

Ring closure of the compound of formula XVII is accomplished by reacting the compound with 1,1'-carbonyldiimidazole and a halogenated aromatic solvent such as o-dichlorobenzene at reflux temperature for about 1 hour to 24 hours, preferably 1 hour to 2 hours. The resultant compound has the structure:

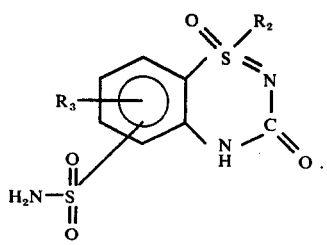
XVIII

Compounds of formula XVIII are novel intermediates and as such they constitute a part of this invention.

The 1,2,4-benzothiadiazine-3(4H)-one-1-oxide of formula XVIII is mixed with benzyl chloroformate and an alkali metal carbonate such as sodium or potassium carbonate in an organic solvent such as acetone and heated under reflux conditions for a period of time of from about 1 hour to 24 hours, preferably 4 hours to 8 hours. The resultant product has the formula:

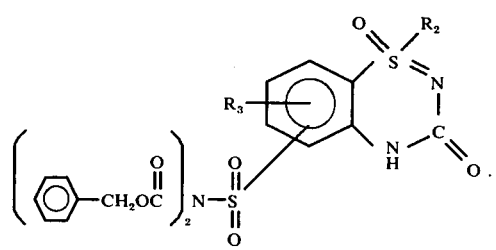
XIX

The compound of formula XIX is reacted with the compound of the formula:

$R_1-X$, (X)

wherein X is halogen, to obtain a compound of the formula:

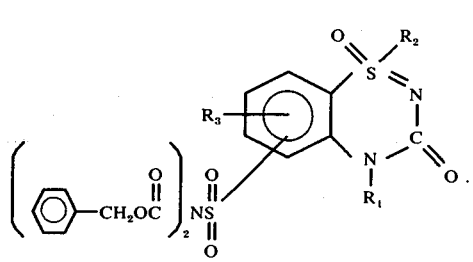
XX

The reaction is carried out by first suspending the compound of formula XIX in a solvent such as glyme and then adding sodium hydride to the suspension at a temperature of about 0° C to 85° C, preferably 0° C to 5° C. The compound of formula X is then slowly added and the reaction mixture is heated under reflux conditions for about 1 hour to 24 hours, preferably 3 hours to 6 hours.

Hydrogenation of the compound of formula XX yields a compound of formula I wherein $R_4$ is

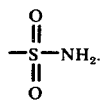

The hydrogenation may be run in absolute alcohol using a platinum oxide catalyst.

To obtain compounds of formula I wherein $R_4$ is

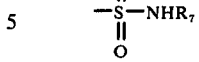

and $R_7$ is lower alkyl, a chlorosulfonyl substituted acetanilide of formula XIII is first prepared as described above. The compound of formula XIII is reacted with an amine having the formula:

$NH_2R_7$ (XXI)

to yield a compound having the formula:

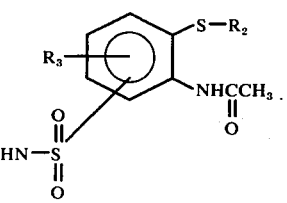
XXII

The reaction can be carried out by first dissolving the compound of formula XIII in an organic solvent, such as benzene, and then adding the solution to an ice-cooled aqueous solution of an amine of formula XXI. After a short period, the reaction mixture is heated under reflux for a period of about 30 minutes to 12 hours, preferably about 1 to 3 hours.

Following the procedure described above for conversion of the sulfamylacetanilide of formula XIV to a sulfamyl substituted 1,2,4-benzothiadiazine of formula I, but substituting the lower alkylsulfamylacetanilide for the sulfamylacetanilide of formula XIV, yields a compound of formula I wherein $R_4$ is

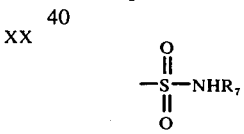

and $R_7$ is lower alkyl.

Formation of the pharmaceutically acceptable acid-addition salts of the compounds of formula I may be accomplished by methods well known in the art. Both organic and inorganic acids are specifically contemplated. Illustrative acids are the hydrohalides, especially the hydrochloride and hydrobromide, sulfate, nitrate, phosphate, tartrate, maleate, fumarate, citrate, succinate, methanesulfonate, benzenesulfonate, toluenesulfonate, and the like.

Compounds having the formula:

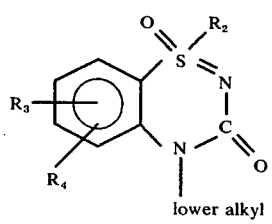
XXIII are specifically contemplated. Examples of the compounds of formula XXIII are 7-chloro-4-methyl-1-(4-methylphenyl)-1,2,4-benzo-
thiadiazin-3(4H)-one, 1-oxide;

6-chloro-4-ethyl-1-(4-ethoxyphenyl)-7-sulfamyl-
1,2,4-benzothiadiazin-3(4H)-one, 1-oxide; and 6-trifluoromethyl-4-propyl-1-phenyl-1,2,4-benzo-
thiadiazin-3(4H)-one, 1-oxide.

Compounds having the formula:

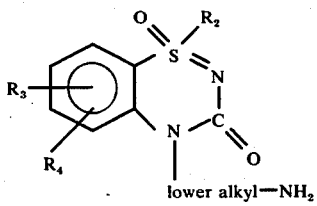
lower alkyl—NH$_2$

XXIV are specifically contemplated. Examples of the compounds of formula XXIV are 7-nitro-4-(3-aminopropyl)-1-phenyl-1,2,4-benzo-
thiadiazin-3(3H)-one, 1-oxide;

7-methyl-4-(2-aminoethyl)-1-phenyl-1,2,4-benzo-
thiadiazin-3(4H)-one, 1-oxide;

4-(3-aminopropyl)-1-(4-trifluoromethylphenyl)-
1,2,4-benzothiadiazin-3(4H)-one, 1-oxide; and 6-methoxy-4-(3-aminopropyl)-1-phenyl-7-sulfamyl-
1,2,4-benzothiadiazin-3(4H)-one, 1-oxide.

Compounds having the formula:

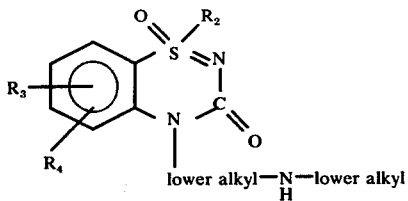
lower alkyl—N—lower alkyl
         H

XXV are specifically contemplated. Examples of the compounds of formula XXV are 7-chloro-4-[3-(methylamino)propyl]-1-phenyl-
1,2,4-benzothiadiazin-3(4H)-one, 1-oxide;

4-[2-(ethylamino)ethyl]-1-phenyl-7-sulfamyl-1,2,4-
benzothiadiazin-3(4H)-one, 1-oxide.

Compounds having the formula:

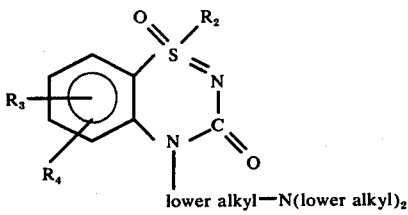
lower alkyl—N(lower alkyl)$_2$

XXVI are specifically contemplated. Examples of the compounds of formula XXVI are 6-methyl-4-[3-(diethylamino)propyl]-1-(3-nitro-
phenyl)-1,2,4-benzothiadiazin-3(4H)-one, 1-oxide;

7-chloro-4-[2-(dimethylamino)ethyl]-1-phenyl-
1,2,4-benzothiadiazin-3(4H)-one, 1-oxide;

4-[2-(diisobutylamino)ethyl]-1-phenyl-1,2,4-benzo-
thiadiazin-3(4H)-one, 1-oxide.

Compounds having the formula:

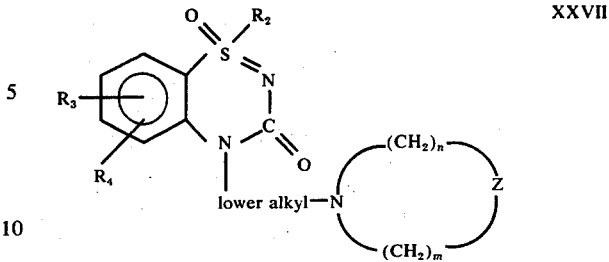

XXVII are specifically contemplated. Examples of the compounds of formula XXVII are 7-chloro-4-[3-(4-piperazino)propyl]-1-phenyl-1,2,4-
benzothiadiazin-3(4H)-one, 1-oxide;

4-[2-(4-morpholino)ethyl]-1-phenyl-7-sulfamyl-
1,2,4-benzothiadiazin-3(4H)-one, 1-oxide.

Compounds wherein R$_2$ is unsubstituted phenyl are preferred.

Compounds wherein R$_3$ is halogen (preferably fluorine, chlorine, or bromine), trifluoromethyl, cyano, and nitro are preferred. Compounds wherein R$_3$ is halogen are especially preferred.

The following examples further illustrate the above described invention.

EXAMPLE 1

7-Chloro-4-[2-(dimethylamino)ethyl]-1-phenyl-1,2,4-
benzothiadiazin-3(4H)-one, 1-oxide A. 4-Chloro-2-(phenylthio)benzoyl chloride To a stirred suspension of 59.2 g (0.224 mole) of 4-chloro-2-(phenylthio)benzoic acid in 200 ml. of benzene is added dropwise 41.6 g (0.35 mole) of thionyl chloride during a 1 hour period, and the reaction mixture is heated under reflux for an additional hour. The reaction mixture is then concentrated to dryness under reduced pressure, and the residue is recrystallized from 300 ml. of boiling hexane to yield 41.9 g. of pale yellow product, melting point 94°–96° C.

Anal. Calcd for $C_{13}H_8Cl_2OS$: C, 55.13; H, 2.85; Cl, 25.04; Found: C, 55.37; H, 2.73; Cl, 24.81.

B. 4-Chloro-2-(phenylthio)acetophenone

A stirred mixture of 3.76 g (0.156 gram-atom) of magnesium turnings, 5 ml. of absolute ethanol, and a few drops of carbon tetrachloride is warmed until the reaction has been initiated. A mixture of 25.0 g. (0.155 mole) of diethylmalonate, 9.3 ml. (0.31 mole in toto) of absolute alcohol, and 150 ml. of anhydrous ether is added rapidly. A gummy reaction product separates from solution. This is heated under reflux conditions for 3 hours. A solution of 39.7 g. (0.14 mole) of 4-chloro-2-(phenylthio)benzoyl chloride in 200 ml. of ether is then run in rapidly from a dropping funnel. After stirring for an additional 3 hours, the complexed addition product is decomposed with a solution of 25 ml. of concentrated sulfuric acid in 200 ml. of water. The addition product is then extracted into 500 ml. of chloroform, and the chloroform extract dried and concentrated to give a solid, melting point 106°–108° C. This solid is heated in a mixture of 20 ml. of concentrated sulfuric acid, 50 ml. of water, and 200 ml. of acetic acid under reflux conditions for 2 hours. The acetic acid is then substantially removed by distillation under reduced pressure. Addition of a further 100 ml. portion of water and cooling leads to crystallization of 35.8 g. of the ketone, melting point 65°–66° C, after recrystallization from aqueous alcohol.

Anal. Calcd for $C_{14}H_{11}ClOS$: C, 63.98; H, 4.22; Cl, 13.40; Found: C, 63.79; H, 4.46; Cl, 13.40.

C. 4-Chloro-2-(phenylsulfinyl)acetophenone

To a vigorously stirred solution of 199 g. (0.75 mole) of 4-chloro-2-(phenylthio)acetophenone in 2 liters of 1,2-dimethoxyethane (glyme) is added a solution of 176.5 g. (0.825 mole) of sodium periodate; the mixture is heated at 40° C for 7 days. The mixture is then filtered from the inorganic materials and the glyme distilled from the filtrate to give a slurry of crystals. These are filtered and this mixture of sulfoxide and starting material is separated from the inorganic contaminants by extraction into abs. ethanol. After filtration and concentration, the residue is dissolved in 1.5 liters of boiling hexane to give (after cooling and filtration) 91.8 g. of product, melting point 129°–130° C.

Anal. Calcd for $C_{14}H_{11}ClO_2S$: C, 60.33; H, 3.97; S, 11.50; Found: C, 60.07; H, 4.18; S, 11.74.

D. 4-Chloro-2-(phenylsulfonimidoyl)acetanilide and 7-Chloro-3-methyl-1-phenyl-1,2,4-benzothiadiazine-1-oxide A stirred, cooled (0° C) solution of 7.0 g. (0.025 mole) of 4-chloro-2-(phenylsulfinyl)acetophenone in 100 ml. of chloroform is combined with 14.0 ml. of concentrated sulfuric acid and treated dropwise with 69 ml. (0.075 mole) of a 1.08 N chloroform solution of hydrazoic acid. After stirring for 1 hour, the ice bath is removed and the mixture is warmed to 40° C; stirring is continued for an additional 30 minutes. The reaction mixture is then cooled, added to 100 ml. of ice water, neutrallized with solid sodium bicarbonate, the chloroform layer separated, and, after drying over anhydrous magnesium sulfate, concentrated to dryness. On recrystallization from aqueous alcohol, the residue gives 3.6 g. of 4-chloro-2-(phenylsulfonimidoyl)acetanilide, melting point 141°–142° C.

Anal. Calcd for $C_{14}H_{13}ClN_2O_2S \cdot \frac{1}{2} H_2O$: C, 52.90; H, 4.44; N, 8.82; S, 10.09;

Found: C, 53.24; H, 4.18; N, 8.45; S, 10.53.

On standing, the mother liquors from the above recrystallization deposit 0.6 g. of 7-chloro-3-methyl-1-phenyl-1,2,4-benzothiadiazine-1-oxide, melting point 151°–152° C.

Anal. Calcd for $C_{14}H_{11}ClN_2OS$: C, 57.84; H, 3.81; N, 9.64 Found: C, 57.75; H, 4.07; N, 9.61.

E. 4-Chloro-2-(phenylsulfonimidoyl)aniline hydrochloride

Following the procedure of (D) but using 83.8 g. (0.30 mole) of 4-chloro-2-(phenylsulfinyl)acetophenone, 500 ml. of chloroform, 250 ml. of concentrated sulfuric acid, and 472 ml. of a 1.4 N chloroform solution of hydrazoic acid, 79.7 g. of a mixture of 4-chloro-2-(phenylsulfonimidoyl)acetonilide and 7-chloro-3-methyl-1-phenyl-1,2,4-benzothiadiazine-1-oxide is obtained. This mixture is stirred and heated under reflux conditions in 450 ml. of 10% sodium hydroxide solution for 3.5 hours. After the mixture is cooled, it is extracted with 500 ml. of chloroform, and the extract is dried and concentrated to give 68.7 g. of a viscous oil. This is extracted with 500 ml. of anhydrous ether. The extract is filtered and cooled in ice. While the extract is cooling on ice, it is treated in a dropwise manner with a slight excess (to pH 4.0) of ethereal hydrogen chloride to give 55.2 g. of product, melting point 217°–219° C after filtration and drying.

F. 7-Chloro-1-phenyl-1,2,4-benzothiadiazin-3(4H)-one, 1-oxide

A stirred mixture of 18.80 g. (0.062 mole) of 4-chloro-2-(phenylsulfonimidoyl)aniline hydrochloride and 10.6 g. (0.065 mole) of 1,1′-carbonyldiimidazole in 500 ml. of o-dichlorobenzene is heated under reflux conditions for 2 hours, filtered, and cooled. The glistening plates which form are filtered, washed with water, and dried to yield 11.28 g. of product, melting point 261°–262° C.

A sample for analysis is recrystallized from alcohol and the melting point is unchanged.

Anal. Calcd for $C_{13}H_{10}ClN_2O_2S$: C, 53.33; H, 3.10; N, 9.57; Found: C, 53.43; H, 3.22; N, 9.74.

G. 7-Chloro-4-[2-(dimethylamino)ethyl]-1-phenyl-1,2,4-benzothiadiazin-3(4H)-one, 1-oxide To a stirred suspension of 6.6 g. (0.0225 mole) of 7-chloro-1-phenyl-1,2,4-benzothiadiazin-3(4H)-one, 1-oxide in 200 ml. of dried and distilled glyme is added (at 0° C) 1.2 g. (0.025 mole) of 50% dispersion of sodium hydride in mineral oil in small portions. After 0.5 hours, 30 ml. of a 1.04 N solution of 2-dimethylaminoethyl chloride (0.031 mole) is added dropwise during a 15 minute period and the mixture is heated under reflux conditions for 6 hours. The reaction mixture is then filtered, and concentrated to dryness to yield 7-chloro-4-[2-(dimethylamino)ethyl]-1-phenyl-1,2,4-benzothiadiazin-3(4H)-one, 1-oxide.

EXAMPLE 2

7-Chloro-4-[2-(dimethylamino)ethyl]-1-phenyl-1,2,4-benzothiadiazin-3(4H)-one, 1-oxide, hydrochloride (1:1)

7-Chloro-4-[2-(dimethylamino)ethyl]-1-phenyl-1,2,4-benzothiadiazin-3(4H)-one, 1-oxide (8.2 grams) is dissolved in 100 ml. of acetonitrile, and treated with 7.5 ml. (0.03 mole) of 4 N ethereal hydrogen chloride. The title compound which is separated is recrystallized 2 times from abs. ethanol and dried at 100° C in vacuo to give 3.0 g. of a colorless product, melting point 261°–262° C, dec.

Anal. Calcd for $C_{17}H_{18}ClN_3O_2S \cdot HCl$: Cl, 17.72; S, 8.01; Found: Cl, 17.92; S, 7.88.

EXAMPLE 3

7-Chloro-4-[3-(dimethylamino)propyl]-1-phenyl-1,2,4-benzothiadiazin-3(4H)-one, 1-oxide, hydrochloride To an ice-cooled, stirred suspension of 11.23 g (0.038 mole) of 7-chloro-1-phenyl-1,2,4-benzothiadiazin-3(4H)-one, 1-oxide (prepared as described in Example 1, parts A–F) in 250 ml of dried and distilled glyme, 2.22 g (0.046 mole) of a 50% dispersion of sodium hydride in mineral oil is gradually added. The mixture is stirred for 30 minutes and then 45.5 ml (0.05 mole of a 1.1 N solution of 3-dimethylaminopropyl chloride is added dropwise over a 15 minute period, followed by heating under reflux conditions for 3 hours. The mixture is filtered, concentrated to dryness, and the residue partitioned between 100 ml of N hydrochloric acid and 100 ml of chloroform. The aqueous phase is separated, made alkaline with sodium bicarbonate, and the product extracted into 250 ml of chloroform. The extract is dried and concentrated to give 11.5 g of the free base of the product in the form of a viscous gum.

Anal. Calcd for $C_{18}H_{20}ClN_3O_2S \cdot 2 H_2O$: C, 52.22; H, 5.84; N, 10.15; Found: C, 51.61; H, 5.35; N, 10.49.

The crude base is dissolved in 50 ml of acetonitrile and cooled in an ice bath. 10 ml of 4N ethereal hydrogen chloride is added dropwise. The solution is concentrated to one-half volume and cooled. The tan colored solid (9.15 g, melting point 227°–229° C, dec.) is filtered and recrystallized from abs. ethanol to give 5.56 g of colorless product, melting point 248°–249° C, dec., after drying at 100° C for 4 hours.

Anal. Calcd for $C_{18}H_{20}ClN_3O_2S \cdot HCl$: C, 52.17; H, 5.11; N, 10.14; Found: C, 51.91; H, 5.20; N, 10.04.

EXAMPLE 4

6-Chloro-4[3-(dimethylamino)propyl]-1-phenyl-7-sulfamyl-1,2,4-benzothiadiazin-3(4H)-one, 1-oxide hydrochloride A. 5-Chloro-2-(phenylthio)acetanilide To a stirred solution of 235.7 g. (1 mole) of 4-chloro-2-(phenylthio)aniline, (prepared by the procedure described in U.S. Pat. No. 3,188,320), in 1 liter of chloroform containing 87.0 g. (1.1 mole) of pyridine, 112.3 g. (1.1 mole) of acetic anhydride is added over a 1 hour period. The mixture is heated under reflux for 1 hour. The cooled reaction mixture is then extracted successively with 1 liter portions of N-hydrochloric acid and N sodium carbonate, dried (anhydrous magnesium sulfate), and concentrated to dryness to give the above product.

B. 5-Chloro-4-chlorosulfonyl-2-(phenylthio)acetanilide

A mixture of 250 g. (0.9 mole) of 5-chloro-2-(phenylthio)acetanilide and 116.52 g. (1.0 mole) of chlorosulfonic acid in 2.5 liters of o-dichlorobenzene is heated at 150°–160° C for 2 hours in an oil bath. The reaction mixture is cooled, washed with 1 liter of cold sodium carbonate solution, washed with water and then dried using magnesium sulfate. Removal of the solvent by distillation under vacuum yields the product.

C. 5-Chloro-2-(phenylthio)-4-sulfamylacetanilide

A solution of 276.0 g. (0.75 mole) of 5-chloro-4-chlorosulfonyl-2-(phenylthio)acetanilide in 2 liters of benzene is added dropwise to 1 liter of concentrated aqueous ammonia, with cooling in an ice bath, over a period of 1 hour. After the addition is complete, the ice bath is removed and the mixture is heated to reflux and stirred vigorously for an additional 2 hours. The benzene is removed by steam distillation, the residual material is cooled, the pH is adjusted to 6.5, and the product is filtered and dried.

D. 5-Chloro-2-(phenylsulfinyl)-4-sulfamylacetanilide 231 g. (0.65 mole) of 5-chloro-2-(phenylthio)-4-sulfamylacetanilide is stirred in 3.5 liters of glyme. A solution of 154 g. (0.72 mole) of sodium periodate in 1500 ml. of water is added to the mixture dropwise over a 2 hour period. The mixture is then stirred vigorously for 24 hours while heating under reflux conditions. The reaction mixture is filtered from the inorganic materials, and concentrated under reduced pressure to remove the glyme. The slurry of crystalline material remaining is cooled, filtered, and the solid material extracted with absolute alcohol, filtered to remove insoluble inorganic contaminants, and the extract partially concentrated, cooled, and filtered to yield the product.

E. 5-Chloro-2-(phenylthiosulfinyl)-4-sulfamylaniline

A solution of 186.8 g. (0.5 mole) of 5-chloro-2-(phenylsulfinyl)-4-sulfamylacetanilide in 1.5 liters of 10% aqueous sodium hydroxide is heated under reflux conditions for 3 hours, cooled, the pH adjusted to 6.5–7 with N hydrochloric acid, and the separated product filtered, dried, and recrystallized from ethanol.

F. 5-Chloro-2-(phenylsulfonimidoyl)-4-sulfamylaniline

A stirred, cooled (0° C) solution of 149.0 g (0.45 mole) of 5-chloro-2-(phenylthiosulfinyl)-4-sulfamylaniline in 1.5 liters of chloroform is combined with 300 ml. of concentrated sulfuric acid and treated dropwise with 450 ml. of a 1 N chloroform solution of hydrazoic acid. After stirring for 1 hour, the ice bath is removed and the mixture is warmed to 40° C; stirring is continued for an additional 30 minutes. The reaction mixture is then cooled, added to 100 ml. of ice water, neutralized with solid sodium bicarbonate, the chloroform layer separated, and, after drying over anhydrous magnesium sulfate, concentrated to dryness. Recrystallization from aqueous alcohol yields the product.

G. 6-Chloro-1-phenyl-7-sulfamyl-1,2,4-benzothiadiazine-3(4H)-one-1-oxide

A stirred mixture of 34.5 g. (0.1 mole) of 5-chloro-2-(phenylsulfonimidoyl)-4-sulfamylaniline and 16.2 g. (0.1 mole) of 1,1'-carbonyldiimidazole in 500 ml. of o-dichlorobenzene is heated under reflux conditions for 2 hours, filtered, and cooled, yielding the product.

H. 6-Chloro-7-(N,N-dibenzyloxycarbonylsulfamyl)-1-phenyl-1,2,4-benzothiadiazine-3(4H)-one-1-oxide A stirred mixture of 37.2 g. (0.1 mole) of 6-chloro-1-phenyl-7-sulfamyl-1,2,4-benzothiadiazine-3(4H)-one-1-oxide, 34.0 g. (0.2 mole) of benzyl chlorformate, 13.8 g. (0.1 mole) of potassium carbonate, and 500 ml. of acetone of heated under reflux conditions for 15 hours, filtered, and concentrated to dryness. The residual material is taken up into 500 ml. of dichloromethane, extracted with 100 ml. of N aqueous sodium hydroxide, washed with water, dried, and concentrated under pressure.

I. 6-Chloro-7-(N,N-dibenzyloxycarbonylsulfamyl)-4-[3-(dimethylamino)propyl]-1-phenyl-1,2,4-benzothiadiazin-3(4H)-one-1-oxide To an ice cooled stirred suspension of 50.6 g (0.08 mole) of 6-chloro-7-(N,N-dibenzyloxycarbonylsulfamyl)-1-phenyl-1,2,4-benzothiadiazine-3(4H)-one-1-oxide in 1 liter of dried and distilled glyme is gradually added 3.7 g. (0.88 mole) of a 57% dispersion of sodium hydride in mineral oil. After stirring for 30 minutes, 140 ml. (0.1 mole) of a 1.4 N solution of dimethylaminopropyl chloride in benzene is added dropwise over a 1 hour period, and the mixture is heated under reflux conditions for 5 hours. It is then filtered, concentrated, and the residue partitioned between 250 ml. of cold N hydrochloric acid and an equal volume of ether. The acid phase is made alkaline with a slight excess of concentrated aqueous ammonia and the product is extracted with two 250 ml. portions of chloroform, the combined extracts dried and concentrated to dryness to yield the product.

J. 6-Chloro-4-[3-(dimethylamino)propyl]-1-phenyl-7-sulfamyl-1,2,4-benzothiadiazin-3(4H)-one-1-oxide A solution of 50.3 g. (0.07 mole) of 6-chloro-7-(dibenzyloxycarbonylsulfamyl)-4-[3-(dimethylamino)propyl]1-phenyl-1,2,4-benzothiadiazin-3(4H)-one-1-oxide in 1 liter of abs. ethanol is hydrogenated at an initial pressure of 50 p.s.i. in the presence of 1.0 g. platinum oxide for 24 hours. The reaction mixture is then filtered, concentrated to dryness under an oil pump vacuum, the residue reprecipitated from dilute aqueous sodium hydroxide solution, filtered, and dried to yield the product.

K. 6-Chloro-4-[3-(dimethylamino)propyl]-1-phenyl-7-sulfamyl-1,2,4-benzothiadiazin-3(4H)-one-1-oxide hydrochloride A solution of 22.8 g. (0.05 mole) 6-chloro-4-[3-(dimethylamino)propyl]-1-phenyl-7-sulfamyl-1,2,4-benzothiadiazin-3(4H)-one-1-oxide in 100 ml. of acetonitrile is treated with 100 ml. of 2.5 N ethereal hydrogen chloride while stirring and cooling in an ice bath. The solid is filtered and dried to yield the product.

EXAMPLE 5

6-Chloro-7-methylsulfamyl-1-phenyl-1,2,4-benzothiadiazin-3(4H)-one, 1-oxide

A. 5-Chloro-4-methylsulfamyl-2-(phenylthio)acetanilide

A solution of 188 g (0.5 mole) of 5-chloro-4-chlorosulfamyl-2-(phenylthio)acetanilide (prepared as described in Example 4, parts A and B) in 1 liter of benzene is added dropwise to 1 liter of ice-cooled, vigorously stirred 40% aqueous methylamine solution over a period of 1 hour. The ice bath is then removed and the reaction mixture is heated under reflux for 2 hours, concentrated under reduced pressure to remove the benzene and excess methylamine, and the pH is adjusted to between 6 and 7 to yield the title compound.

B. 5-Chloro-4-methylsulfamyl-2-(phenylsulfinyl)acetanilide

To a solution of 148 g. (0.4 mole) of 5-chloro-4-methylsulfamyl-2-(phenylthio)acetanilide in 1 liter of acetic acid is added 37.5 ml. (0.44 mole) of a 40% solution of hydrogen peroxide over a 1 hour period while stirring vigorously. The mixture is allowed to stand for 24 hours, and then poured into 5 liters of ice water to yield the title compound.

C. 5-Chloro-4-methylsulfamyl-2-(phenylsulfinyl)aniline

A solution of 116 g. (0.3 mole) of 5-chloro-4-methylsulfamyl-2-(phenylsulfinyl)acetanilide in 1 liter of 10% sodium hydroxide solution is heated under reflux conditions for 3 hours, cooled, and the pH adjusted to 6.5 with 20% hydrochloric acid to yield the title compound.

D. 5-Chloro-4-methylsulfamyl-2-(phenylsulfonimidoyl)aniline

To a stirred, cooled (0° C) mixture of 69.0 g. (0.25 mole) of 5-chloro-4-methylsulfamyl-2-(phenylsulfinyl)aniline, 1 liter of chloroform and 200 ml. of concentrated sulfuric acid is added 250 ml. of a N solution of hydrazoic acid in chloroform over a 2 hour period. After stirring for 3 hours, 500 g. of crushed ice is added, the reaction mixture is neutralized with sodium bicarbonate, the chloroform layer is separated, and the residual material is extracted 3 times with 500 ml. portions of chloroform. After drying, the chloroform solutions are combined and concentrated to dryness to yield the title compound.

E. 6-Chloro-7-methylsulfamyl-1-phenyl-1,2,4-benzothiadiazine-3(4H)-one, 1-oxide

A stirred solution of 5-chloro-4-methylsulfamyl-2-(phenylsulfonimidoyl)aniline and 16.2 g. (0.1 mole) of 1,1'-carbonyldiimidazole in 500 ml. of o-dichlorobenzene is heated under reflux for 2 hours in a nitrogen atmosphere, filtered while hot and then cooled to yield the title compound.

EXAMPLES 6–14

Following the procedure of Example 1, parts A through G, but substituting the compounds indicated in Column I below for 2-dimethylaminoethyl chloride in Example 1, part G, the compounds indicated in Column II are obtained.

| Example | Column I | Column II |
| --- | --- | --- |
| 6 | 2-(4-phenylpiperidino)ethyl chloride | 7-chloro-4-[2-(4-phenylpiperidino)ethyl]-1-phenyl-1,2,4-benzothiadiazin-3(4H)-one, 1-oxide |
| 7 | 3-(4-phenylpiperazino)propyl chloride | 7-chloro-4-[3-(4-phenylpiperazino)propyl]-1-phenyl-1,2,4-benzothiadiazin-3(4H)-one, 1-oxide |
| 8 | 2-(4-methylpiperazino)ethyl chloride | 7-chloro-4-[2-(4-methylpiperazino)ethyl]-1-phenyl-1,2,4-benzothiadiazin-3(4H)-one, 1-oxide |
| 9 | 2-[4-(2-methoxyphenyl)piperazino]ethyl chloride | 7-chloro-4-[2-[4-(2-methoxyphenyl)piperazino]ethyl]-1-phenyl-1,2,4-benzothiadiazin-3(4H)-one, 1-oxide |
| 10 | 2-morpholino-ethyl chloride | 7-chloro-4-[2-(morpholino)ethyl]-1-phenyl-1,2,4-benzothiadiazin-3(4H)-one, 1-oxide |
| 11 | 2-pyrrolidino-ethyl chloride | 7-chloro-4-[2-(pyrrolidino)ethyl]-1-phenyl-1,2,4-benzothiadiazin-3(4H)-one, 1-oxide |
| 12 | methyl iodide | 7-chloro-4-methyl-1-phenyl-1,2,4-benzothiadiazin-3(4H)-one, 1-oxide |
| 13 | 3-aminopropyl chloride | 7-chloro-4-[3-(amino)propyl]-1-phenyl-1,2,4-benzothiadiazin-3(4H)-one, 1-oxide |
| 14 | 2-ethylaminoethyl chloride | 7-chloro-4-[2-(ethylamino)ethyl]-1-phenyl-1,2,4-benzothiadiazin-3(4H)-one, 1-oxide. |

EXAMPLES 15–33

Following the procedure of Example 1, parts A through G, but substituting the compounds indicated in Column I below for 4-chloro-2-(phenylthio)benzoic acid in Example 1, part A, and the compounds indicated in Column II below for 2-dimethylaminoethyl chloride in Example 1, part G, the compounds indicated in Column III are obtained.

| Example | Column I | Column II | Column III |
| --- | --- | --- | --- |
| 15 | 4-(trifluoromethyl)-2-(phenylthio)benzoic acid | dimethylaminopropyl chloride | 7-(trifluoromethyl)-4-[3-(dimethylamino)propyl]-1-phenyl-1,2,4-benzothiadiazin-3(4H)- |

-continued

| Example | Column I | Column II | Column III |
|---|---|---|---|
| 16 | 5-chloro-2-(phenylthio)benzoic acid | dimethylaminopropyl chloride | 6-chloro-4-[3-(dimethylamino)propyl]-1-phenyl-1,2,4-benzothiadiazin-3(4H)-one, 1-oxide |
| 17 | 4-nitro-2-(phenylthio)benzoic acid | dimethylaminopropyl chloride | 7-nitro-4-[3-(dimethylamino)propyl]-1-phenyl-1,2,4-benzothiadiazin-3(4H)-one, 1-oxide |
| 18 | 4-(trifluoromethyl)-2-(phenylthio)benzoic acid | methylaminopropyl chloride | 7-(trifluoromethyl)-4-[3-(methylamino)propyl]-1-phenyl-1,2,4-benzothiadiazin-3(4H)-one, 1-oxide |
| 19 | 4-nitro-2-(phenylthio)benzoic acid | methylaminopropyl chloride | 7-nitro-4-[3-(methylamino)propyl]-1-phenyl-1,2,4-benzothiadiazin-3(4H)-one, 1-oxide |
| 20 | 4-methyl-2-(phenylthio)benzoic acid | methylaminopropyl chloride | 7-methyl-4-[3-(methylamino)propyl]-1-phenyl-1,2,4-benzothiadiazin-3(4H)-one, 1-oxide |
| 21 | 4-chloro-2[(2-chlorophenyl)thio]benzoic acid | methylaminopropyl chloride | 7-chloro-4-[3-(methylamino)propyl]-1-(2-chlorophenyl)-1,2,4-benzothiadiazin-3(4H)-one, 1-oxide |

What is claimed is:
1. A compound having the structure:

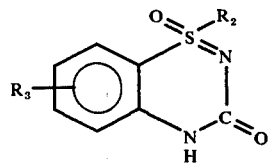

wherein $R_2$ is phenyl, or phenyl substituted with halogen, nitro, trifluoromethyl, lower alkyl or lower alkoxy; and $R_3$ is hydrogen, halogen, nitro, trifluoromethyl, lower alkyl or lower alkoxy.

2. A compound having the structure:

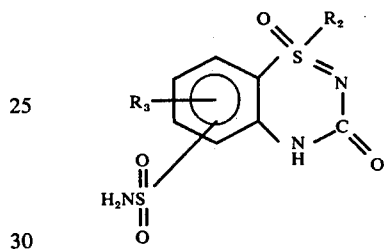

wherein $R_2$ is phenyl, or phenyl substituted with halogen, nitro, trifluoromethyl, lower alkyl or lower alkoxy; and $R_3$ is hydrogen, halogen, nitro, trifluoromethyl, lower alkyl or lower alkoxy.

3. The compound in accordance with claim 1 having the name 7-chloro-1-phenyl-1,2,4-benzothiadiazin-3(4H)-one-1-oxide.

4. The compound in accordance with claim 2 having the name 6-chloro-1-phenyl-7-sulfamyl-1,2,4-benzothiadiazin-3(4H)-one-1-oxide.

* * * * *